United States Patent [19]

DeBernardis et al.

[11] Patent Number: 4,634,705

[45] Date of Patent: Jan. 6, 1987

[54] ADRENERGIC AMIDINES

[75] Inventors: John F. DeBernardis, Lake Villa; Fatima Z. Basha, Lake Bluff, both of Ill.

[73] Assignee: Abbott Laboratories, North Chicago, Ill.

[21] Appl. No.: 838,212

[22] Filed: Mar. 7, 1986

Related U.S. Application Data

[63] Continuation-in-part of Ser. No. 617,770, Jun. 6, 1984, abandoned.

[51] Int. Cl.[4] .................. A61K 31/505; C07D 239/06
[52] U.S. Cl. ..................................... 514/256; 514/394; 514/396; 514/397; 514/400; 514/401; 514/402; 514/411; 514/452; 514/463; 514/604; 514/605; 514/637; 544/242; 544/333; 544/335; 548/326; 548/336; 548/346; 548/347; 548/348; 548/427; 549/359; 549/433; 564/82; 564/83; 564/92; 564/99; 564/244; 564/247
[58] Field of Search ............... 548/326, 427, 346, 336, 548/347, 348; 549/359, 433; 514/394, 452, 411, 256, 396, 397, 400, 401, 402, 463, 604, 605, 637; 544/242, 333, 335; 564/82, 83, 92, 99, 244, 247

[56] References Cited

U.S. PATENT DOCUMENTS 3,354,175 11/1967 Fruhstorfer et al. ............... 548/347
4,499,105 2/1985 Panneman ..................... 564/244 X

FOREIGN PATENT DOCUMENTS 877306 9/1961 United Kingdom ............... 548/347

Primary Examiner—Richard A. Schwartz
Attorney, Agent, or Firm—Steven F. Weinstock; Martin L. Katz

[57] ABSTRACT

Disclosed herein are adrenergic compounds represented by the formula

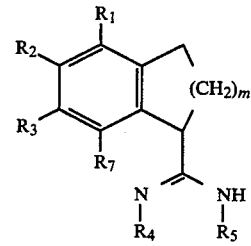

wherein m is 0, 1 or 2; $R_1$, $R_2$, $R_3$ and $R_7$ are taken from the group consisting of hydrogen, hydroxy, loweralkyl, loweralkoxy, halo, amino, acetamido or $NHSO_2R$ wherein R is taken from the group consisting of hydrogen or loweralkyl, provided that $R_1$, $R_2$, $R_3$ and $R_7$ cannot simultaneously be hydrogen or halo, and provided that when one of $R_1$, $R_2$, $R_3$ and $R_7$ is halo, the others cannot simultaneously be hydrogen and when two of $R_1$, $R_2$, $R_3$ and $R_7$ are halo, the other two cannot simultaneously be hydrogen and provided that $R_1$ and $R_7$ cannot simultaneously be methoxy each when $R_2$ and $R_3$ are hydrogen; $R_1$ and $R_2$ or $R_2$ and $R_3$ or $R_3$ and $R_7$ taken together can form a methylenedioxy or ethylenedioxy bridge; or $R_1$ and $R_2$ or $R_2$ and $R_3$ or $R_3$ and $R_7$ taken together with the aromatic ring can form a benzimidazole or indole bridge; and $R_4$ and $R_5$ are hydrogen or taken together form a closed ring of the formula

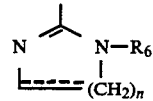

wherein n is 1 or 2, and the combined solid and dashed line represents a single or double bond when n is 1, and $R_6$ is taken from the group consisting of hydrogen or loweralkyl, and the pharmaceutically acceptable salts thereof.

15 Claims, No Drawings

ADRENERGIC AMIDINES

BACKGROUND OF THE INVENTION

This application is a continuation-in-part of application Ser. No. 617,770 filed June 6, 1984, now abandoned.

This invention relates to novel adrenergic compounds useful in the treatment of hypertension, depression, nasal congestion, metabolic disorders (e.g. obesity) and migraine.

The adrenergic nervous system plays a major role in the innervation of heart, blood vessel and smooth muscle tissue. Compounds capable of interacting with receptor sites within the adrenergic nervous system can initiate a variety of physiological responses, including vasoconstriction, vasodilation, and increased or decreased heart rate (chronotropic), contractility (inotropic) and metabolic activity. In the past, various adrenergic compounds have been employed to affect these and other physiological responses. However, many adrenergic compounds do not possess significant selectivity to enable desirable interactions with adrenergic receptor sites. That is, these adrenergic compounds do not demonstrate a high degree of specificity for differing receptor types within the adrenergic nervous system in order to obtain a desired physiological response separate from other possible, and perhaps less desirable, responses of the system. It has now been determined that a new class of compounds, as herein defined, demonstrate an ability to selectivity stimulate (agonists) or inhibit (antagonists) α-adrenergic receptors which are mainly distributed on the membranes of central and peripheral adrenergic neurons and on the tissues innervated thereby.

Through inhibitory interaction with the α-adrenergic receptor in the peripheral nervous system, one can modulate the function of adrenergic neurons and hemodynamic equilibrium which is therapeutically useful in a multitude of cardiovascular indications such as hypertension, congestive heart failure, and a variety of vascular spastic conditions. Stimulatory interaction with α-adrenergic receptors in the peripheral nervous system is therapeutically useful in situations where vascular constrictions such as nasal, otic or ophthalmic congestion and inflammation occur.

In the central nervous system, stimulatory α-adrenergic receptor agonists are therapeutically useful for sedation, diuresis, and in treatment of additive behavior and hypertension. The α-adrenergic antagonists in the central nervous system are useful in certain neurological and psychiatric disorders such as depression as well as for maintenance of cardiovascular equilibrium.

The therapeutic usefulness of the compounds of this invention stems from their selectivity for adrenergic receptor subtypes and their selective modulation of the adrenergic function in different tissues or organs.

DISCLOSURE OF THE INVENTION

The present invention provides compounds represented by the formula (I)

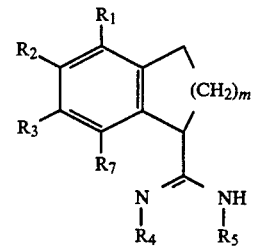

wherein m is 0, 1 or 2; $R_1$, $R_2$, $R_3$ and $R_7$ are taken from the group consisting of hydrogen, hydroxy, loweralkyl, loweralkoxy, halo, amino, acetamido or $NHSO_2R$ wherein R is taken from the group consisting of hydrogen or loweralkyl, provided that $R_1$, $R_2$, $R_3$ and $R_7$ cannot simultaneously be hydrogen or halo, and provided that when one of $R_1$, $R_2$, $R_3$ and $R_7$ is halo, the others cannot simultaneously be hydrogen and when two of $R_1$, $R_2$, $R_3$ and $R_7$ are halo, the other two cannot simultaneously be hydrogen and provided that $R_1$ and $R_7$ cannot simultaneously be methoxy each when $R_2$ and $R_3$ are hydrogen; $R_1$ and $R_2$ or $R_2$ and $R_3$ or $R_3$ and $R_7$ taken together can form a methylenedioxy or ethylenedioxy bridge; or $R_1$ and $R_2$ or $R_2$ and $R_3$ or $R_3$ and $R_7$ taken together with the aromatic ring can form a benzimidazole or indole bridge; and $R_4$ and $R_5$ are hydrogen or taken together form a closed ring of the formula

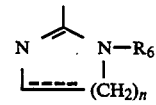

wherein n is 1 or 2, and the combined solid and dashed line represents a single or double bond when n is 1, and $R_6$ is taken from the group consisting of hydrogen or loweralkyl, and the pharmaceutically acceptable salts thereof.

As used herein, the term "loweralkoxy" refers to alkoxy groups containing from 1 to 6 carbon atoms in straight or branched chains with or without double bonds, i.e., methoxy, ethoxy, propoxy, isopropoxy, butoxy, allyloxy, etc.

The term "loweralkyl" means straight or branched chain saturated hydrocarbon radicals having 1 to 6 carbon atoms, such as methyl, ethyl, n-propyl, iso-propyl, n-butyl, s-butyl, and t-butyl.

The term "pharmaceutically acceptable salts" refers to the pharmaceutically acceptable, relatively nontoxic, inorganic or organic acid addition salts of the compounds of this invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerate, oleate, palmitrate, stearate, laurate, borate, benzoate, lactate, phosphate, tosylate, citrate, maleate, fumarate, succinate, tartrate, napsylate and the like. It will be apparent to those skilled in the art that, depending upon the number of available amino groups for salt formation, the salt of this invention can be per-N-salts.

The foregoing may be better understood in connection with the following examples:

EXAMPLE 1

1-Cyano-5,6-dimethoxy-(3,4-dihydronaphthalene)

5,6-dimethoxytetralone (20 g) was dissolved in benzene (20 ml) and trimethylsilyl cyanide (16 ml). A catalytic amount of aluminum chloride was added and the reaction heated at 70° C. under nitrogen for 30 minutes. The volatiles were removed in vacuo and methanol (20 ml) added. Gaseous hydrochloric acid was bubbled through the methanol solution for 30 minutes resulting in precipitation of a solid. Stirring was continued for 1 hour, then the mixture was filtered and dried affording 19.9 g. of product (96% yield); m.p. 138°–9° C.

EXAMPLE 2

1-Cyano-5,6-dimethoxy-(1,2,3,4-tetrahydronaphthalene)

The product from Example 1 (10.5 g) was refluxed for 2.5 hours in ethanol (200 ml) containing sodium borohydride (6 g). The reaction was cooled to room temperature and evaporated to dryness. Aqueous hydrochloric acid (50 ml) was carefully added followed by extraction with dichloromethane. The organic layer was separated, dried and evaporated affording 8.4 g. of the desired product (79% yield); m.p. 50°–1° C.

EXAMPLE 3

Ethyl 5,6-dimethoxy-(1,2,3,4-tetrahydronaphthalene)-1-carboximidate

1-Cyano-5,6-dimethoxy-(1,2,3,4-tetrahydronaphthalene (15 g) was dissolved in 140 ml diethylether and then ethanol (70 ml) added. The solution was cooled to 0° C. and hydrochloric acid bubbled through for 2 hours. The reaction was allowed to warm to room temperature, stoppered tightly and allowed to stand at room temperature overnight. The solvent was evaporated, then acetonitrile added followed again by evaporation of the volatiles. The oily residue was taken up in acetonitrile (25 ml) and the product was precipitated by addition of diethylether (200 ml) to this solution. The product was filtered and air dried giving 14.5 g.; m.p. 137–8(d).

EXAMPLE 4

5,6-Dimethoxy-2'-(1,2,3,4-tetrahydro-1-naphthyl)-imidazoline HCl

The product from Example 3 (2.0 g) was dissolved in ethanol (25 ml) and cooled to 0° C. Ethylene diamine (1.8 ml) was added dropwise to this solution and upon complete addition stirring was continued for 1 hour at 0° C. The reaction was then allowed to warm to room temperature overnight. The solvent was removed in vacuo giving an oil. Water (50 ml) was added followed by a diethylether extraction (70 ml), then a dichloromethane extraction (100 ml). The organic extracts were separated, combined, dried and evaporated giving an oil which solidified upon standing (1.7 g). This material was dissolved in ether (5 ml) and added to ethereal hydrochloric acid (15 ml) and the resulting salt filtered and dried; m.p. 245°–7° C.

EXAMPLE 5

5,6-Dihydroxy-2'-(1,2,3,4-tetrahydro-1-naphthyl)imidazoline HBr

The product from Example 4 (1.7 g) was dissolved in dichloromethane (50 ml) and cooled to −78° C. under nitrogen. Borontribromide (2.4 ml) in 10 ml dichloromethane was added dropwise to this solution, and upon complete addition the reaction was stirred at room temperature for 2 hours. This was then cooled to −78° C. and excess borontribromide quenched by dropwise addition of methanol (25 ml). Upon complete addition of the methanol, the mixture was allowed to warm to room temperature and stirred for 1 hour. The solution was evaporated in vacuo affording a solid; m.p. 268°–70° C.

EXAMPLE 6

1-Cyano-5,6-methylenedioxy-(3,4-dihydronaphthylene)

Utilizing the procedure of Example 1 but replacing the 5,6-dimethoxy-1-tetralone with 5,6-methylenedioxy-1-tetralone afforded the desired product; m.p. 82°–83° C.

EXAMPLE 7

1-Cyano-5,6-methylenedioxy-(1,2,3,4-tetrahydronaphthalene)

The product from Example 6 was reduced using the procedure of Example 2 to afford the product in 98% yield.

EXAMPLE 8

Ethyl 5,6-methylenedioxy-(1,2,3,4-tetrahydronaphthylene)-1-carboximidate

The product from Example 7 (3.8 g) was dissolved in absolute ethanol (30 ml) and diethylether (60 ml) and the imino ether formed as in Example 3 affording the product in 87% yield; m.p. 185°–87° C.

EXAMPLE 9

5,6-Methylenedioxy-2'-(1,2,3,4-tetrahydro-1-naphthyl)imidazoline HCl

Using the product from Example 8 and the procedure of Example 4 afforded the desired product as the monohydrate; m.p. 264°–65° C.

EXAMPLE 10

1-Cyano-6,7-dimethoxy-(1,2,3,4-tetrahydronaphthalene)

Starting with 1-cyano-6,7-dimethoxy-(3,4-dihydronaphthylene) (17.7 g) and using the procedure of Example 2 afforded the desired compound in 98% yield as an oil.

EXAMPLE 11

Ethyl, 6,7-dimethoxy(1,2,3,4-tetrahydronaphthylene)-1-carboximidate

The product from Example 10 (15 g) was reacted as in Example 3 to afford the desired product (18.8 g) in 92% yield; m.p. 179°–82° C.

EXAMPLE 12

6,7-Dimethoxy-2'-(1,2,3,4-tetrahydronaphthyl)imidazoline HCl

The product from Example 11 (2.5 g) was dissolved in ethanol (30 ml) and reacted with ethylenediamine (1.2 ml) as in Example 4 giving the desired product; m.p. 253°-4° C.

EXAMPLE 13

6,7-Dihydroxy-2'-(1,2,3,4-tetrahydro-1-naphthyl)imidazoline HBr

The product from Example 12 (1.2 g) was reacted with boronitribromide (1.5 ml) as in Example 5 affording the product; m.p. 260°-61° C.

EXAMPLE 14

1-Cyano-5-methoxy-(3,4-dihydronaphthalene)

Trimethylsilyl cyanide (28.2 g) and a catalytic amount of aluminum trichloride was added to a toluene solution of 5-methoxy-1-tetralone (25 g) and the reaction heated for 2 hours. The solution was evaporated to dryness. Pyridine (100 ml) was then added, followed by dropwise addition of phosphorous oxychloride (40 ml). Upon complete addition the reaction was heated to 120° C. for 2 hours. The reaction was cooled and poured onto ice containing aqueous hydrochloric acid. The mixture was extracted with ether (100 ml). The organic layer was separated, dried, filtered and evaporated affording the desired product as an oil which solidified upon standing.

EXAMPLE 15

1-Cyano-5-methoxy-(1,2,3,4-tetrahydronaphthalene)

The product from Example 14 (11.4 g) was refluxed for 2.5 hours in ethanol (250 ml) containing sodium borohydride (3.0 g). The reaction was cooled to room temperature and evaporated to dryness. Aqueous hydrochloric acid (50 ml) was carefully added followed by extraction with dichloromethane. The organic layer was separated, dried and evaporated affording the product (9.2 g).

EXAMPLE 16

Ethyl-5-methoxy-(1,2,3,4-tetrahydronaphthalene)-1-carboximidate

The product from Example 15 (4.7 g) was dissolved in ethanol (50 ml) and ether (50 ml). The solution was cooled to 0° C. and hydrochloric acid (g) bubbled through this for 2 hours. The reaction was allowed to warm to room temperature, stoppered tightly and allowed to stand at room temperature overnight. The solvent was evaporated. Acetonitrile was then added, followed again by evaporation of the volatiles. The oily residue was taken up in acetonitrile (25 ml) and the product precipitated by addition of diethylether (200 ml). The product was filtered and air dried affording the desired product.

EXAMPLE 17

5-Methoxy-2'-(1,2,3,4-tetrahydro-1-naphthyl)imidazoline, HCl

The product from Example 16 (5.9 g) was dissolved in ethanol (50 ml) and cooled to 0° C. Ethylene diamine (5.4 ml) was added dropwise to this solution and upon complete addition, stirring was continued for 1 hour at 0° C. and then at room temperature overnight. The solvent was evaporated to dryness. The residue was taken up in ether. Ethereal hydrochloric acid was then added. The hydrochloric acid salt was filtered and dried; m.p. 198°-99° C.

EXAMPLE 18

5-Hydroxy-2'-(1,2,3,4-tetrahydro-1-naphthyl)imidazoline HBr

The product from Example 17 (1.6 g) was dissolved in methylene chloride (25 ml) and cooled to −78° C. under nitrogen. Boron tribromide (2.7 ml) in 5 ml methylene chloride was added dropwise to this solution and upon complete addition, the reaction was stirred at room temperature for 2 hours. After this time, the reaction was cooled to −78° C. and quenched by the dropwise addition of methanol (25 ml). The solution was evaporated to dryness and the residue crystallized from an ethanol-ether mixture affording the product; m.p. 229°-30° C.

EXAMPLE 19

6-Methoxy-2'-(1,2,3,4-tetrahydro-1-naphthyl)imidazoline HCl

1-Cyano-6-methoxy-(1,2,3,4-tetrahydronaphthalene) (5.25 g) and the mono paratoluene sulfonate salt of ethylenediamine (20.9 g) was heated to 250° C. in a flask under nitrogen, for ca. 4 minutes. The reaction was cooled to room temperature and a solid mass resulted. This solid was dissolved in 6N hydrochloric acid (ca. 250 ml) and extracted with diethylether (3×150 ml). The aqueous layer was separated and made basic with sodium hydroxide, followed by methylene chloride extraction (3×100 ml). The organic layers were combined, dried, filtered and evaporated to dryness giving an oily residue. This residue was dissolved in ethanol (25 ml) and ethereal hydrochloric acid added. Evaporation to dryness gave a glass which upon trituration with acetonitrile afforded a solid; m.p. 182°-184° C.

EXAMPLE 20

6-Hydroxy-2'-(1,2,3,4-tetrahydro-1-naphthyl)imidazoline HBr

The product from Example 19 (1.2 g) was suspended in methylene chloride (20 ml) and cooled to −78° C. Boron tribromide (2.5 ml) in methylene chloride (5 ml) was added dropwise. Upon complete addition, reaction was allowed to warm to room temperature and stirred for 2 hours. The reaction was then cooled to −78° C. and quenched by the dropwise addition of methanol (25 ml), followed by evaporation to dryness. The resulting solid was crystallized from ethanol/acetonitrile mixture affording the desired product; m.p. 254°-55° C.

EXAMPLE 21

7-Methoxy-2'-(1,2,3,4-tetrahydro-1-naphthyl)imidazoline HCl

Ethyl-7-methoxy(1,2,3,4-tetrahydronaphthalene)-1-carboximidate (6 g) was dissolved in 50 ml ethanol and reaction cooled to 0° C., followed by the dropwise addition of ethylenediamine (5.4 ml). The reaction was stirred at room temperature overnight, then evaporated to dryness affording a wax. The wax was suspended in water and extracted with diethylether. The ether solubles were washed with brine, separated and dried. Evaporation gave a glass, to which methanolic hydrochloric acid was added. The solution was evaporated to dryness and diethylether and a few drops of acetonitrile added. The light yellow solid was filtered and dried; m.p. 162°–63° C.

EXAMPLE 22

7-Hydroxy-2'-(1,2,3,4-tetrahydro-1-naphthyl)imidazoline HBr

The product from Example 21 (0.68 g) was suspended in methylene chloride (20 ml) and then cooled to −10° C. Boron tribromide (1.4 ml) in methylene chloride (5 ml) was added dropwise. After the addition, the reaction was allowed to warm to room temperature and stirred for 2 hours. The reaction was cooled to −78° C. and quenched with methanol. Evaporation of the solvents gave a white solid which was slurried in ether, then filtered; m.p. 255°–56° C.

EXAMPLE 23

5-Methoxy-2'-(1-indanyl)imidazoline HCl

1-Cyano-5-methoxy indane was dissolved in 30 ml ethanol and 30 ml diethylether, and gassed with dry hydrochloric acid for 25 minutes and then allowed to stand in a stoppered flask at room temperature overnight. The solvents were removed, then ethylenediamine (3.0 g) and ethanol (50 ml) were added, and the reaction heated for 30 minutes and evaporated to dryness. The residue was taken up in ethanol (10 ml) and ethereal hydrochloric acid added. The solution was evaporated to dryness affording the product as a glass.

EXAMPLE 24

5-Hydroxy-2'-(1-indanyl)imidazoline HBr

The product from Example 23 (1.5 g) was dissolved in methylene chloride (20 ml), then cooled to −78° C. followed by the dropwise addition of $BBr_3$ in 5 ml methylene chloride. The reaction was allowed to warm to room temperature for 2 hours, then cooled to −78° C. and quenched with methanolic hydrochloric acid (20 ml). Evaporation of the solvents afforded a solid which was crystallized from methanol; m.p. 283°–84° C.

EXAMPLE 25

Ethyl-4,5-dimethoxy-indane-1-carboximidate

1-Cyano-4,5-dimethoxy-(2,3-dihydroindane) (4.5 g), ethanol (50 ml) and diethylether (50 ml) were combined, then cooled to −78° C., followed by gassing with dry hydrochloric acid for 30 minutes. After this time, the reaction was allowed to stand at room temperature for 22 hours, and the solvents removed, affording a solid.

EXAMPLE 26

4,5-Dimethoxy-2'-(1-indanyl)-imidazoline HCl

The product from Example 25 (4.3 g) was dissolved in ethanol (50 ml) and ethylenediamine (8.5 ml) and the reaction was stirred at room temperature overnight, followed by heating for 30 minutes. Evaporation of the solvents afforded an oil, which solidified upon standing. This was crystallized from acetonitrile affording a white solid. This was dissolved in ethanol (10 ml) and ethereal hydrochloric acid added. The resulting hydrochloric acid salt was recrystallized from acetonitrile affording the product; m.p. 226°–227° C.

EXAMPLE 27

4,5-Dihydroxy-2'-(1-indanyl)imidazoline HBr

The product from Example 26 (0.6 g) was dissolved in methylene chloride (20 ml) and cooled to −78° C. Boron tribromide (2 ml) in methylene chloride (5 ml) was then added dropwise. The reaction was allowed to warm to room temperature overnight, then quenched with methanol (25 ml). Evaporation afforded a grayish solid, which was washed with ether to give a white solid; m.p. 239°–240° C.

EXAMPLE 28

5,6-Dimethoxy-2'-(1,2,3,4-tetrahydro-1-naphthyl)-pyrimidine HCl

To an ethanol (20 ml) solution of ethyl-5,6-dimethoxy-(1,2,3,4-tetrahydronaphthylene)-1-carboximidate was added 1,3-diaminopropane (1.25 ml) and the reaction refluxed one hour. The solution was evaporated to dryness and aqueous potassium hydroxide (50 ml) added, followed by methylene chloride (200 ml) extraction. The organic layer was separated, dried, filtered and then methanolic hydrochloric acid added. The solution was evaporated to dryness. Methylene chloride was then added. Diethylether was added until the product began to crystallize from solution; m.p. 208°–9° C.

EXAMPLE 29

5,6-Dihydroxy-2'-(1,2,3,4-tetrahydro-1-naphthyl)-pyrimidine HBr

The product from Example 28 (1.0 g) was dissolved in methylene chloride (30 ml) and cooled to −78° C. Then boron tribromide (1.2 ml) in methylene chloride (5 ml) was added dropwise. Upon complete addition, the reaction was allowed to warm to room temperature, then stirred for 1 hour. The reaction was cooled to −78° C. and quenched with methanol (20 ml). Evaporation afforded a solid which was crystallized from a methanol/ether mixture giving the product; m.p. 221°–3° C.

EXAMPLE 30

5,6-Dimethoxy-2'-(1,2,3,4-tetrahydro-1-napthyl)-imidazole HCl

Ethyl-5,6-dimethoxy-(1,2,3,4-tetrahydronaphthyl)-1-carboximidate (3 g) was dissolved in ethanol (30 ml), then aminoacetaldehyde diethylacetal (1.8 ml) was added and the solution refluxed for 16 hours. The solvent was evaporated and 4N hydrochloric acid (50 ml) added, followed by heating at 60° C. for 24 hours. The reaction was cooled, 45% potassium hydroxide added and solids precipitated. The solid was filtered, washed with water and dried. Methylene chloride was added to dissolve the solid and then ethereal hydrochloric acid afforded the product; m.p. 168°–69° C.

EXAMPLE 31

5,6-Dihydroxy-2'-(1,2,3,4-tetrahydro-1-naphthyl)-imidazole.HBr

The product from Example 30 (1.03 g) was dissolved in methylene chloride (30 ml), then cooled to −78° C. and boron tribromide (1.3 ml) in methylene chloride (5 ml) added dropwise. The reaction was then allowed to reach room temperature. After 30 minutes a solid precipitated. The reaction was cooled to −78° C. and quenched with methanol (30 ml). An initial solution

EXAMPLE 32

5,6-Dimethoxy-(1,2,3,4-tetrahydronaphthyl)-1-carboxamidine.HCl

Ethyl-5,6-dimethoxy-(1,2,3,4-tetrahydronaphthyl)-1-carboximidate (1.0 g) in ethanol (30 ml) was refluxed overnight with ammonium hydroxide (10 ml). The solvents were then removed under vacuum. The solid was converted to the hydrochloric acid salt affording the desired product.

EXAMPLE 33

5,6-Dihydroxy-(1,2,3,4-tetrahydronaphthyl)-1-carboxamidine.HBr

The product from Example 32 (0.65 g) was dissolved in methylene chloride (30 ml) and the boron tribromide (1.1 ml) in methylene chloride (5 ml) added dropwise. The procedure of Example 5 was then followed, affording the desired product; m.p. 270°–72° C.

EXAMPLE 34

4,5-Methylenedioxy-2'-(1-indanyl)imidazoline HCl

Utilizing the procedure from Example 4 with 4,5-methylenedioxy indanyl-1-carboximidate (2.1 g) in ethanol (15 ml) and ethylenediamine (1 ml) afforded the desired product; m.p. 221°–23° C.

EXAMPLE 35

5-Methoxy-6-hydroxy-2'-(1,2,3,4tetrahydro-1-naphthyl)imidazoline HCl 1-cyano-5-methoxy-6-hydroxy-(1,2,3,4-tetrahydronaphthalene (0.9 g) was dissolved in methanol (10 ml), diethylether (30 ml) and methylene chloride (30 ml) and cooled in an ice/isopropanol bath. The solution was then gassed with dry hydrogen chloride for 30 minutes, stoppered tightly, and allowed to stand overnight at room temperature.

The solvent was removed and the resulting solid taken up in methanol (20 ml) followed by the addition of ethylenediamine (0.75 ml). The solution was refluxed for 3 hours, then stripped to dryness. The residue was dissolved in ethanol (5 ml). Then ethereal hydrochloric acid was added. The resulting hydrochloride salt was filtered and recrystallized from a mixture of ethanol and diethylether affording the product; m.p. 165°–66° C.

EXAMPLE 36

5-hydroxy-6-methoxy-2'-(1,2,3,4-tetrahydro-1-naphthyl)imidazoline HCl

Utilizing the procedure of Example 35, with 1-cyano-5-benzyloxy-6-methoxy-(1,2,3,4-tetrahydronaphthalene) (1.5 g) and ethylenediamine (0.97 ml) gave the desired product; m.p. 258°–59° C.

EXAMPLE 37

6-hydroxy-7-methoxy-2'-(1,2,3,4-tetrahydro-1-naphthyl)imidazoline HCl

Using the procedure from Example 35 with 1-cyano-6-benzyloxy-7-methoxy-(1,2,3,4-tetrahydronaphthylene) (2.4 g) and ethylenediamine (1.06 ml) afforded the desired product; m.p. 295°–96° C.

EXAMPLE 38

6-methoxy-7-hydroxy-2'-(1,2,3,4-tetrahydro-1-naphthyl)imidazoline HCl

Using the procedure from Example 35 with 1-cyano-6-methoxy-7-hydroxy-(1,2,3,4-tetrahydronaphthylene (2.4 g) and ethylenediamine (2 ml) gave the compound; m.p. 243°–44° C.

EXAMPLE 39

5-bromo-6-methoxy-2'-(1,2,3,4-tetrahydro-1-naphthyl)imidazoline HCl

Using the procedure from Example 35 with 1-cyano-5-bromo-6-methoxy-(1,2,3,4-tetrahydronaphthylene) (1.5 g) and ethylenediamine (0.97 ml) afforded the desired product; m.p. 273°–74° C.

EXAMPLE 40

5-bromo-6-hydroxy-2'-(1,2,3,4-tetrahydro-1-naphthyl)imidazoline HBr

Using the procedure of Example 5 with the product from Example 39 (0.65 g) afforded the desired compound; m.p. 253°–54° C.

EXAMPLE 41

Methyl-3,4-dimethoxy-benzocyclobutane-1-carboximidate

Hydrogen chloride gas was bubbled into a 0° C. solution of methanol (10 ml) diethylether (50 ml), and methylenechloride (50 ml) containing 1-cyano-3,4-dimethoxy-benzocyclobutane (5 g). After 15 minutes the flask was stoppered and kept in the refrigerator overnight. The solvents were evaporated and the residue triturated with $CH_2Cl_2$ (ca. 100 ml) affording a white solid; m.p. 207°–8° C.

EXAMPLE 42

3,4-Dimethoxy-2'-(1-benzocyclobutane)-imidazoline HCl

An ethanol (40 ml) suspension of the product from Example 41 was treated with ethylenediamine (2 ml). The reaction was stirred at room temperature for 2.5 hours. The solvent was removed and the oily residue partitioned between water and methylene chloride. The organic layer was separated, dried (magnesium sulfate), filtered, and evaporated, affording the amine. This was taken up in isopropyl alcohol (50 ml) and then isopropyl alcohol (3 ml) saturated with hydrogen chloride gas was added. The resulting hydrochloride salt was filtered and air dried; m.p. 214°–15° C.

EXAMPLE 43

3,4-Dihydroxy-2'-(1-benzocyclobutane)-imidazoline HBr

Using the procedure of Example 5 and the product from Example 42 gave the product which was recrystallized from ethanol; m.p. 225° C. (d).

EXAMPLE 44

5,7-Dimethoxy-2'-(1,2,3,4-tetrahydro-1-naphthyl)imidazoline HCl

Utilizing the procedure from Example 35 with 1-cyano-5,7-dimethoxy-1,2,3,4-tetrahydronaphthalene (2.0 g.) and ethylenediamine (1.5 ml.) gave the compound; m.p. 173°–174° C.

EXAMPLE 45

5,7-Dihydroxy-2'-(1,2,3,4-tetrahydro-1-naphthyl-)imidazoline HBr

Utilizing the procedure from Example 5 with the product from Example 44 (0.82 g.) afforded the desired compound; m.p. 263°–64° C.

EXAMPLE 46

5,6,7-Trimethoxy-2'-(1,2,3,4-tetrahydro-1-naphthyl-)imidazoline HCl

Utilizing the procedure from Example 35 with 1-cyano-5,6,7-trimethoxy-1,2,3,4-tetrahydronaphthalene (2.7 g.) and ethylenediamine (1.06 ml.) gave the compound; m.p. 185°–86° C.

EXAMPLE 47

5,6,7-Trihydroxy-2'-(1,2,3,4-tetrahydro-1-naphthyl-)imidazoline HBr

Utilizing the procedure from Example 5 with the product from Example 46 (1.0 g.) gave the compound; m.p. 252°–53° C.

EXAMPLE 48

5-Allyloxy-2'-(1,2,3,4-tetrahydro-1-naphthyl)imidazoline HCl

Utilizing the procedure of Example 35 with 1-cyano-5-allyloxy-1,2,3,4-tetrahydronaphthalene (2.8 g.) and ethylenediamine (2.4 ml.) gave the compound; m.p. 184°–85° C.

EXAMPLE 49

1-Cyano-5,7-dimethyl-(3,4-dihydronaphthalene)

Utilizing the procedure of Example 14 but replacing the 5-methoxy-1-tetralone with 5,7-dimethyl-1-tetralone afforded the desired product in 60% yield.

EXAMPLE 50

1-Cyano-5,7-dimethyl-(1,2,3,4-tetrahydronaphthalene)

The product from Example 49 was reduced using the procedure of Example 2 to afford the desired material in 71% yield.

EXAMPLE 51

2-(1,2,3,4-Tetrahydro-4,7-dimethyl-1-naphthalene)imidazoline-HCl

Utilizing the procedure from Example 35 with the product from Example 50 (3.0 g) afforded the desired compound; m.p. 269°–270° C.

EXAMPLE 52

1-Fluoro-2-methoxy-3-[(2-propenyl)oxy]benzene

A mixture of 3-fluoro-2-methoxyphenol (19.5 g; 0.137 m) potassium carbonate (85 g), allyl bromide (15 ml) and acetone (100 ml) was refluxed for 4 hours. The reaction was cooled to room temperature and evaporated to dryness. The residue was partitioned between water and dichloromethane. The organic layer was separated, dried and evaporated affording 19.0 g of the desired product as an oil.

EXAMPLE 53

3-Fluoro-2-methyoxy-6-(2-propenyl)phenol

The product from Example 52 without purification was subjected to Claisen Rearrangement, which required heating the product of example 52 (10.3 g) at 200° C. for 8 hours. After flash chrmatographic separation, the desired O-allyl product was obtained in 71% yield as an oil.

EXAMPLE 54

1-Fluoro-2,3-dimethoxy-4-(2-propenyl)benzene

The product from Example 53 (7.4 g) was treated with 60% NaH (3.0 g) in DMF (200 ml) for 1 hour and methyl iodide (6 ml) added. The reaction was stirred for another hour, poured onto ice/water and extracted with ethyl acetate. The organic layer was separated dried and evaporated affording 7.3 g of the desired product (90%) yield as an oil.

EXAMPLE 55

4-Fluoro-2,3-dimethoxybenzene butanal

The product from Example 54 (7.2 g) was treated with 9-BBN (85 ml, 0.5M in THF) at room temperature with stirring for 2 hours. The stirring was stopped and the reaction mixture cooled to 0° then potassium triisopropoxyborohydride (43 ml, 1.0M in THF) was added. Carbon monoxide was bubbled through the reaction mixture for 3 hours, then pH 7 buffer (60 ml) and 30% $H_2O_2$ (16 ml) was added with stirring and the reaction was allowed to stir overnight. The reaction mixture was quenched with water, and extracted with ethyl acetate. The organic layer was separated, dried and evaporated to afford the desired product as an oil.

EXAMPLE 56

4-Fluoro-2,3-dimethoxybenzene butanoic acid

The product from Example 55 (12.6 g) was oxidized with silver oxide prepared in situ from a solution of silver nitrate (15.6 g) in $H_2O$ (22 ml) and potassium hydroxide (12.7 g) in $H_2O$ (22 ml). The reaction was done in ethanol (170 ml) with stirring at room temperature. After 1 hour, the precipitated silver salts were filtered, washed with water and concentrated to ½ volume. The aqueous basic layer was diluted with water extracted with hexane several times, acidified and extracted with ethyl acetate. The organic layer was separated, dried and evaporated to afford the acid in 30% yield.

EXAMPLE 57

5,6-Dimethoxy-7-fluoro-1-tetralone

The product from Example 56 (3.6 g) was added to PPA (35 g) and the syrup was heated for 5 min on a steam bath. The reaction mixture was poured onto ice water and extracted with methylene chloride. The organic layer was separated, washed with aqueous sodium bicarbonate solution, dried and evaporated. The residue was purified using flash chromatography to afford the desired compound in 30% yield.

EXAMPLE 58

1-Cyano-5,6-dimethoxy-7-fluoro-(3,4-dihydronaphthalene)

Utilizing the procedure of Example 1 but replacing the 5,6-dimethoxy-1-tetralone with 5,6-dimethoxy-7-fluoro-1-tetralone afforded the desired product in 60% yield.

EXAMPLE 59

1-Cyano-5,6-dimethoxy-7-fluoro-(1,2,3,4-tetrahydronaphthalene)

The product from Example 58 was reduced using the procedure of Example 2 to afford the product in 83% yield.

EXAMPLE 60

5,6-Dimethoxy-7-fluoro-2'-(1,2,3,4-tetrahydro-1-naphthalenyl)imidazoline HCl

Using the product from Example 59 and the procedure from Example 35 afforded the desired compound in 60% yield. M+@278.

EXAMPLE 61

2-(1,2,3,4-Tetrahydro-5,6-dihydroxy-7-fluoro-1-naphthalenyl)imidazoline HBr

The product from Example 60 (0.3 g) was reacted with borontribromide (0.5 ml) as in Example 5 affording the product as the monohydrate; m.p. 226°–228° C.

EXAMPLE 62

1-Fluoro-3-methoxy-4-[(2-propenyl)oxy]benzene

A solution of 4-fluoro-2-methoxyphenol (27.0 g) in DMF (50 ml) was added dropwise to a mixture of 60% NaH (7.0 g) in DMF (250 ml). After stirring the reaction for 1 hour, allylbromide (21.0 ml) was added and stirring was continued for 1 hour at room temperature. The reaction was poured onto ice/water and extracted with ethyl acetate. The organic layer was separated, dried and evaporated to afford the desired compound.

EXAMPLE 63

4-Fluoro-2-methoxy-6-(2-propenyl)phenol

Utilizing the procedure from Example 53 with the product from Example 62 (36 g) afforded the desired compound as an oil in 60% yield.

EXAMPLE 64

1-Fluoro-3,4-dimethoxy-5-(2-propenyl)benzene

The product from Example 63 (25 g) was alkylated utilizing the procedure outlined in Example 54 to afford (11 g) of desired material in 45% yield.

EXAMPLE 65

5-Fluoro-2,3-dimethoxybenzene butanal

The product from Example 64 (11 g) was functionalized to the desired homologated aldehyde utilizing the procedure from Example 55. The desired compound was obtained in 80% yield.

EXAMPLE 66

5-Fluoro-2,3-dimethoxybenzene butanoic acid

The product from Example 65 (11 g) was oxidized as in Example 56 to afford the desired product (7.4 g) in 62% yield.

EXAMPLE 67

5,6-Dimethoxy-8-fluoro-1-tetralone

The product from Example 66 (7.4 g) was cyclized with methanesulfonic acid (75 ml) at room temperature overnight. The reaction was poured onto water and extracted with methylene chloride. The organic layer was separated, washed with brine, dried and evaporated to afford 4.7 g impure tetralone. Purification was achieved by extraction with hot hexane to obtain 3.7 g pure compound.

EXAMPLE 68

1-Cyano-5,6-dimethoxy-8-fluoro-(3,4-dihydronaphthalene)

The product from Example 67 (3.7 g) was treated with trimethylsilyl cyanide (5 ml) using the procedure of Example 1 and afforded the desired product (2.5 g) in 62% yield.

EXAMPLE 69

1-Cyano-5,6-dimethoxy-8-fluoro-(1,2,3,4-tetrahydronaphthalene)

The product from Example 68 (2.5 g) was reduced with sodium borohydride (1.3 g) using the procedure of Example 2 to afford the product (1.65 g) in 66% yield.

EXAMPLE 70

5,6-Dimethoxy-8-fluoro-2'-(1,2,3,4-tetrahydro-1-naphthyl)imidazoline HCl

Using the procedure of Example 35 with the product from Example 69 (0.8 g) afforded the desired compound (0.7 g) in 75% yield. M+@278.

EXAMPLE 71

2-(8-Fluoro-1,2,3,4-tetrahydro-5,6-dihydroxy-1-naphthalenyl)imidazoline HBr

Utilizing the procedure from Example 5 with the product from Example 70 (0.7 g) gave the compound as the monohydrate; m.p. 258°–60° C.

EXAMPLE 72

6-Acetamido-1-cyano-(3,4-dihydronaphthalene)

6-Acetamido-1-tetralone (4 g) was suspended in benzene (20 ml) and trimethylsilyl cyanide (3.2 ml) added. A catalytic amount of aluminum chloride was added and the reaction heated at 80° C. under nitrogen for 3 hours, then additional trimethylsilyl cyanide (3.2 ml) was added and reaction heated to 110° for 1 hour. The volatiles were removed in vacuo and the residue purified on a short silica column to afford the trimethylsilyl cyanide adduct 4.75 g (79%) which was dissolved in toluene (150 ml). A catalytic amount of p-toluenesulfonic acid was added and the reaction mixture was refluxed for 1 hour, cooled, and the solvent evaporated. The residue was dissolved in ethyl acetate and washed successively with 5% NaHCO$_3$, brine, dried and evaporated to yield 2.9 g of a brown oil.

EXAMPLE 73

6-Acetamido-1-cyano-(1,2,3,4-tetrahydronaphthalene)

The product from Example 72 was reduced using the procedure of Example 2 to afford the product in 41% yield.

EXAMPLE 74

2-(6-Acetylamino-1,2,3,4-tetrahydro-1-naphthalenyl)imidazoline HCl

The product from Example 73 (0.6 g) was dissolved in freshly distilled dimethoxyethane (30 ml) and methanol (2 ml) and cooled to 0° C. The solution was then gassed with dry hydrogen chloride for 30 minutes, stoppered tightly, and allowed to stand overnight at room temperature.

The solvent was removed and the residue suspended in ethanol (25 ml) followed by the addition of ethylenediamine (2 ml). The resulting solution was stirred at room temperature for 3 hours, concentrated and poured into 5% NaHCO₃, then extracted with methylene chloride. The aqueous layer was made strongly basic with concentrated sodium hydroxide solution and extracted with methylene chloride. The organic layer was separated, dried and evaporated to dryness. The residue was dissolved in ethanol (5 ml), then ethereal hydrochloric acid was added. The crystalline salt was filtered (0.5 g); m.p. 226°–29° C.

EXAMPLE 75

2-(6-Amino-1,2,3,4-tetrahydro-1-naphthalenyl)imidazoline 2HCl

The product from Example 74 (1 g) was dissolved in 6N hydrochloric acid (20 ml) and heated to 90° C. for 1 hour. The reaction mixture was cooled and basified with aqueous sodium hydroxide and extracted with methylene chloride. The organic layer was separated, dried and evaporated to afford a white amorphous solid (0.76 g). The solid was dissolved in methylene chloride and treated with ethereal hydrochloric acid. The resulting hydrochloride salt was recrystallized from a mixture of ethanol and diethylether affording the product (0.9 g) in 94% yield; m.p. >295° C.

EXAMPLE 76

O-(1-Cyano-1,2,3,4-tetrahydro-6-methoxy-5-nitro-1-naphthalenyl)O,O-diethyl phosphate 6-Methoxy-5-nitro-1-tetralone (1.1 g) was suspended in tetrahydrofuran (20 ml) at 0° C. then lithium cyanide (0.1 g) and diethyl cyanophosphonate (0.9 ml) were added and the reaction stirred at 0° C. for 1 hour. The solvent was evaporated and the residue dissolved in ethyl acetate then washed with brine, dried, and stripped to afford 1.89 g (98%) of a yellow crystalline product.

EXAMPLE 77

5-Amino-6-methoxy-1-cyano-(1,2,3,4-tetrahydronaphthalene)

The product from Example 76 (7.18 g) was hydrogenated in ethyl acetate (2 L) with 10% Pd/C (dry), 3 atmospheres at room temperature. The catalyst was filtered, and the ethyl acetate layer was extracted 3 times with 10% hydrochloric acid solution. The acidic layer was cooled, basified with ammonium hydroxide and the precipitated product was filtered to afford 2.56 g of the desired product (68% yield).

EXAMPLE 78

1-Cyano-6-methoxy-5-methylsulfonylamino-(1,2,3,4-tetrahydronaphthalene)

A solution of the product from Example 77 (2.5 g) in pyridine (10 ml) was treated with methanesulfonyl chloride (2 ml). After 4 hours stirring at room temperature the reaction was diluted with water and the mixture was filtered and dried affording 2.76 of product (80% yield).

EXAMPLE 79

2-(1,2,3,4-Tetrahydro-6-methoxy-5-methylsulfonylamino-1-naphthylalenyl)imidazoline Using the product from Example 78 (1.4 g) and the procedure of Example 74 afforded the desired product (0.87 g).

EXAMPLE 80

2-(1,2,3,4-Tetrahydro-6-hydroxy-5-methylsulfonylamino-1-naphthalenyl)imidazoline HBr The product from Example 79 (0.85 g) was reacted with borontribromide (2.2 ml) as in Example 5 affording the crude product. The hydrobromide salt was recrystallized from a mixture of ethanol and diethylether affording the product 0.49 g in 69% yield; m.p. 263°–5° C. (decomp).

EXAMPLE 81

6-Acetamido-5-nitro-1-tetralone

6-Acetamido-tetralone (15 g) was added in small portions to a cold solution of nitric acid (46 ml) at −30° C. After the addition was complete (2–3 hours), the reaction mixture was stirred at the same temperature for 1 hour, warmed to 0° C. and stirred for 4 hours. The reaction was poured on ice, basified with aqueous sodium hydroxide and extracted with ethyl acetate several times. The organic layer was separated, dried and evaporated. The desired 5-nitro-isomer was separated using flash chromatography (ethyl acetate-methylene chloride) to afford 8.73 g (48%).

EXAMPLE 82

6-Amino-5-nitro-1-tetralone

The product from Example 81 (1 g) was treated with 6N hydrochloric acid (30 ml) at reflux for 2 hours and the reaction cooled then basified with ammonium hydroxide. The desired product was filtered, washed and dried.

EXAMPLE 83

6-Amino-1-cyano-5-nitro-(1,2,3,4-tetrahydronaphthalene)

Utilizing the procedure of Example 1 but replacing the 5,6-dimethoxy-1-tetralone with 6-amino-5-nitro-tetralone afforded the desired product after column purification (methylene chloride-ethyl acetate; 9:1).

EXAMPLE 84

6-Amino-1-cyano-5-nitro-(1,2,3,4-tetrahydronaphthalene)

The product from Example 83 (0.53 g) was reduced using the procedure of Example 2 to afford the product in 80% yield.

EXAMPLE 85

Cyano-5,6-diamino-(1,2,3,4-tetrahydronaphthalene)

The product from Example 84 (0.5 g) was dissolved in methanol and treated with Pt/C and hydrogen for 3 hours. The solvent was evaporated affording the product in 100% yield.

EXAMPLE 86

6,7,8,9-Tetrahydro-3H-naphth[1,2-d]imidazole-6-carbonitrile

A mixture of the product from Example 85 (0.45 g), 4N hydrochloric acid (8 ml) and formic acid (0.2 ml) was heated to reflux for 45 minutes. The reaction mixture was cooled to 0° C., and basified with ammonium hydroxide and extracted with ethyl acetate. The organic layer was separated, dried and evaporated in vacuo affording the desired material in 90% yield.

EXAMPLE 87

6-(4,5-Dihydro-1H-imidazol-2-yl)-6,7,8,9-tetrahydro-3H-naphth[1,2-d]imidazole 2HCl Utilizing the procedure of Example 35, with the product from Example 86 (1.35 g) afforded the desired compound as the dihydrochloride 1.16 g (50% yield) m.p. 197° (decomp).

EXAMPLE 88

1-Cyano-6-methylsulfonylamine-(3,4-dihydronaphthalene)

6-Methylsulfonylamine-1-tetralone (3.58 g) was reacted as in Example 1 to afford the desired product (3.52 g) in 95% yield.

EXAMPLE 89

1-Cyano-6-methylsulfonylamine-(1,2,3,4-tetrahydronaphthalene)

The product from Example 88 (3.52 g) was reduced with sodium borohydride (3.5 g) using the procedure of Example 2 to afford the desired product (3.35 g) in 95% yield.

EXAMPLE 90

2-(1,2,3,4-Tetrahydro-6-methylsulfonylamino-1-naphthalenyl)imidazoline HCl

Using the procedure from Example 35 with 1-cyano-6-methylsulfonylamine-(1,2,3,4-tetrahydronaphthalene) (3.33 g) and ethylenediamine (7 ml) gave the compound; (1.5 g) m.p. 247°-249° C.

EXAMPLE 91

5-Chloro-1-cyano-6-methoxy-(3,4-dihydronaphthalene)

Starting with 5-chloro-6-methoxy-1-tetralone (1.9 g) and using the procedure of Example 1 afforded the desired compound in 83% yield as a white crystalline solid.

EXAMPLE 92

5-Chloro-1-cyano-6-methoxy-(1,2,3,4-tetrahydronaphthalene)

The product from Example 91 (1.66 g) was reduced using the procedure of Example 2 to afford the desired product in 100% yield.

EXAMPLE 93

2-(5-Chloro-1,2,3,4-tetrahydro-6-methoxy-1-naphthalenyl)imidazoline HCl

Utilizing the procedure of Example 35 with 5-chloro-1-cyano-6-methoxy-(1,2,3,4-tetrahydronaphthalene) (1.6 g) and ethylenediamine (5 ml) gave the compound; m.p. 278°-80° C.

EXAMPLE 94

2-(5-Chloro-1,2,3,4-tetrahydro-6-hydroxy-1-naphthalenyl)imidazoline HBr

The product from Example 93 (0.9 g) was dissolved in methylene chloride (75 ml) and borontribromide (1.1 ml) added dropwise. The procedure of Example 5 was then followed, affording the desired product; m.p. >290°.

EXAMPLE 95

5,7-Dichloro-6-hydroxy-1-tetralone

A solution of 6-hydroxy-1-tetralone (1.62 g) in chloroform (100 ml) was treated with t-butyl hypochlorite (2.3 ml) dropwise at room temperature. After 1.5 hours the reaction was diluted with chloroform and quenched with aqueous sodium bisulfite. The organic layer was separated, washed with brine, dried and evaporated in vacuo affording the desired product in 96% yield. Recrystallized from hot ethyl acetate yielded (1 g) of needles.

EXAMPLE 96

5,7-Dichloro-6-methoxy-1-tetralone

A mixture of the product from Example 95 (2.31 g), potassium carbonate (1.6 g) and DMF (20 ml) was stirred at 50° C. then methyl iodide (0.93 ml) was added. An additional 1.6 ml methyl iodide was added over the next 20 minutes. After 1 hour at 50° C. the reaction was quenched with water and extracted with methylene chloride. The organic layer was separated, dried and evaporated affording the product in 90% yield.

EXAMPLE 97

1-Cyano-5,7-dichloro-6-methoxy-(3,4-dihydronaphthalene)

The product from Example 96 (0.2 g) was dissolved in tetrahydrofuran (15 ml), cooled to −15° C. and treated with lithium cyanide (20 mg) and diethyl cyanophosphonate (0.2 ml). After 30 minutes, the reaction was quenched with water and extracted with ethyl acetate. The organic layer was separated, dried and the solvent evaporated. The residue was dissolved in benzene (30 ml) and a catalytic amount of p-toluenesulfonic acid was added. The reaction was refluxed for 30 minutes, quenched with 5% sodium bicarbonate, and extracted with ether. The organic layer was separated, dried and the solvent evaporated in vacuo affording the desired product in 95% yield.

EXAMPLE 98

1-Cyano-5,7-dichloro-6-methoxy-(1,2,3,4-tetrahydronaphthalene)

The product from Example 97 (3.35 g) was reduced using the procedure of Example 2 to afford the desired product in 95% yield.

EXAMPLE 99

2-(5,7-Dichloro-(1,2,3,4-tetrahydro-6-methoxy-1-naphthalenyl)imidazoline HCl

Utilizing the procedure of Example 35 with 1-cyano-5,7-dichloro-6-methoxy-(1,2,3,4-tetrahydronaphthalene) (1.2 g) and ethylenediamine (3 ml) gave the compound, m.p. 209°-11° C.

EXAMPLE 100

2-(5,7-Dichloro-1,2,3,4-tetrahydro-6-hydroxy-1-naphthalenyl)imidazoline HBr

The product from Example 99 (1.39 g) was dissolved in methylene chloride (100 ml) and borontribromide (1.5 ml) was added dropwise at −78° C. The procedure of Example 5 was then followed to afford the desired product in 80% yield; m.p. 282°–84° C.

EXAMPLE 101

3-Methyl-4-nitro-γ-oxobenzene butanoic acid, ethyl ester

4-Methyl-γ-oxobenzene butanoic acid ethyl ester (10.1 g) was dissolved in concentrated sulfuric acid (30 ml) and cooled to 0° C. After 10 minutes, the reaction was quenched with ice and extracted with diethylether. The organic layer was separated and washed with 5% sodium bicarbonate, brine and dried. The solvent was evaporated in vacuo affording the desired compound in 90% yield.

EXAMPLE 102

4-(Acetylamino)-3-methylbenzenebutanoic acid ethyl ester

The product from Example 101 (18.05 g) was dissolved in ethyl acetate (1 L) and subjected to hydrogenation with 20% Pd/C (dry) in the presence of acetic anhydride (15 ml). The reaction mixture was filtered, and the solvent was evaporated. The residue was dissolved in ethanol (250 ml) and a catalytic amount of sulfuric acid (5 drops) was added. The resulting solution was hydrogenated at room temperature overnight. The catalyst was filtered and the filtrate was washed with 5% sodium bicarbonate dried and the solvent was evaporated to afford the desired compound in 90% yield.

EXAMPLE 103

3-Acetylamino-4-methylbenzene butanoic acid

The product from Example 102 (1.31 g) was dissolved in methanol (10 ml) and water (5 ml). The mixture was treated with 50% sodium hydroxide 0.4 g) and was stirred at room temperature for 18 hours. The reaction was diluted with water and extracted with ether. The aqueous basic layer was acidified and the precipitated acid was collected, washed with water and air dried to afford the desired compound in 80% yield.

EXAMPLE 104

6-Acetylamino-7-methyl-1-tetralone

The product from Example 103 (0.9 g) was added to polyphosphoric acid (20 g) at 100° C. After stirring for 30 minutes at 100° C. the reaction was poured onto ice/water and extracted with ethyl acetate. The organic layer was separated, dried and evaporated to afford the desired product in 68% yield.

EXAMPLE 105

6-Amino-7-methyl-1-tetralone

The product from Example 104 (0.44 g) was hydrolyzed using the procedure of Example 82 to afford the product in 96% yield.

EXAMPLE 106

6-Amino-1-cyano-7-methyl-(3,4-dihydronaphthalene)

Using the product from Example 105 (1.12 g) and the procedure of Example 1 afforded the desired product in 95% yield.

EXAMPLE 107

6-Amino-1-cyano-7-methyl-(1,2,3,4-tetrahydronaphthalene)

The product from Example 106 (1.13 g) was reduced using the procedure of Example 2 to afford the product in 70% yield.

EXAMPLE 108

2-(6-Amino-1,2,3,4-tetrahydro-7-methyl-1-naphthalenyl)imidazoline HCl

Utilizing the procedure from Example 74 and the product from Example 107 (0.74 g) gave the desired compound in 70% yield. m.p. >300° C.

EXAMPLE 109

6-Amino-5-chloro-7-methyl-1-tetralone

The product from Example 105 (0.175 g) was dissolved in tetrahydrofuran (5 ml) and was treated with t-butyl hypochlorite (0.12 ml). Following the procedure of Example 95 the desired product was obtained in 90% yield.

EXAMPLE 110

6-Amino-5-chloro-1-cyano-7-methyl-(3,4-dihydronaphthalene)

Utilizing the procedure of Example 1 but replacing the 5,6-dimethyoxy-1-tetralone with 6-amino-5-chloro-7-methyl-1-tetralone (0.1 g) afforded the desired compound in 80% yield.

EXAMPLE 111

6-Amino-5-chloro-1-cyano-7-methyl-(1,2,3,4-tetrahydronaphthalene)

The product from Example 110 (0.5 g) was reduced using the procedure of Example 2 to afford the product in 90% yield.

EXAMPLE 112

2-(6-Amino-5-chloro-1,2,3,4-tetrahydro-7-methyl-1-naphthalenyl)imidazoline HCl

The product from Example 111 (0.77 g) was reacted as in Example 74 to afford the desired compound (0.87 g) in 85% yield; m.p. >280° C.

EXAMPLE 113

2,3-Dihydro-7-(2-propenyl)-1H-indole

A mixture of 2,3-dihydro-1-(2-propenyl)-1H-indole (1.59 g), tetralin (25 ml) and borontrifluoride etherate (1.3 ml) was heated at 200° C. for 1.5 hours. The reaction mixture was cooled to room temperature then quenched with 10% sodium carbonate and extracted with ethyl acetate. The organic layer was separated, washed with brine, dried and evaporated. The residue was chromatographed over silica (ethyl acetate-hexane 15:85) affording 1.23 g of the desired product (77% yield).

EXAMPLE 114

2,3-Dihydro-7-(2-propenyl)-1H-indole-1-carboxylic acid, ethyl ester

The product from Example 113 (0.8 g) was dissolved in pyridine (3 ml), cooled to 0° C. and ethyl chloroformate (0.77 ml) was added. After 10 minutes, the reaction was quenched with water and extracted with diethylether. The organic layer was separated and washed with cold 2% hydrochloric acid, 5% sodium bicarbonate, brine and dried. The solvent was evaporated in vacuo affording the desired compound in 90% yield as an oil.

EXAMPLE 115

1-(Ethoxycarbonyl)-2,3-dihydro-1H-indole-7-butanoic acid, ethyl ester

The product from Example 114 (4.73 g) was reacted as in Example 55 and 56 to afford the desired product (3.46 g) in 61% yield as an oil.

EXAMPLE 116

2,3,6,7,8,9-Hexahydro-6-oxo-1H-benz[g]-indole-1-carboxylic acid, ethyl ester

The product from Example 115 (2.7 g) was dissolved in benzene (25 ml) and oxalyl chloride (2.6 ml) was added. The resulting solution was heated at 50° C. for 30 minutes, then the solvent was evaporated to dryness. The residue was dissolved in methylene chloride (30 ml), cooled to 0° C., and aluminum chloride (4 g) was added. The reaction mixture was stirred at 0° C. for 1 hour then quenched with ice and hydrochloric acid then extracted with methylene chloride. The organic layer was separated, washed with brine, dried and evaporated in vacuo affording the desired product in 50% yield.

EXAMPLE 117

O-[1-(Ethoxycarbonyl)-6-cyano-2,3,6,7,8,9-hexahydro-1H-benz[g]indol-6-yl]O,O-diethyl phosphate The product from Example 116 (52 mg) was dissolved in tetrahydrofuran (1 ml). The procedure of Example 76 was then followed to afford the desired compound in 90% yield.

EXAMPLE 118

6-Cyano-2,3,6,7,8,9-Hexahydro-1H-benz[g]indole-1-carboxylic acid, ethyl ester

Using the product from Example 117 (1.7 g) and the procedure of Example 77 afforded the desired product in 82% yield.

EXAMPLE 119

2,3,6,7,8,9-Hexahydro-6-(4,5-dihydro-1H-imidazol-2-yl)-1H-benz[g]indole-1-carboxylic acid, ethyl ester Utilizing the procedure of Example 35, with the product from Example 118 (0.8 g) afforded the desired compound in 65% yield.

EXAMPLE 120

2,3,6,7,8,9-Hexahydro-6-(4,5-dihydro-1H-imidazol-2-yl)-1H-benz[g]indole

A solution of the product from Example 119 (0.38 g) in 6N hydrochloric acid (40 ml) was refluxed for 14 hours. The reaction mixture was cooled to 0° C., basified to pH 11 and extracted with methylene chloride. The organic layer was separated, dried and evaporated to afford the desired compound.

EXAMPLE 121

1,3,8,9-tetrahydro-1-methylthio-2H-benz[e]indole-2,6(7H)-dione

A solution of ethyl (methyl thio) acetate (6 g) in methylene chloride (20 ml) was added dropwise to a solution of chlorine (2 ml) in methylene chloride (100 ml) at −78° C. To this colorless solution was added a solution of 6-amino-1-tetralone (6.4 g) in methylene chloride (170 ml) and triethyl amine (5.6 ml) dropwise over 30 minutes. After stirring the reaction mixture at −70° C. for 5 hours a solution of triethyl amine (8 ml) in methylene chloride (20 ml) was added and the reaction was warmed to room temperature and quenched with water. The aqueous layer was extracted with methylene chloride and the organic layer was stirred with 2.5N hydrochloric acid (100 ml) overnight. The organic layer was separated, dried and evaporated to afford the desired compound after triturating with diethylether in 50% yield.

EXAMPLE 122

1,2,8,9-Tetrahydro-1-(methylthio)-2-oxo-3H-benz[e]indole-6-carbonitrile

The product from Example 121 (4.9 g) was reacted as in Example 1 to afford the desired product (4 g) in 78% yield.

EXAMPLE 123

6,7,8,9-Tetrahydro-1-(methylthio)-3H-benz[e]indole-6-carbonitrile

The product from Example 122 (4 g) was reduced using the procedure of Example 2 to afford the desired compound in 50% yield.

EXAMPLE 124

6,7,8,9-Tetrahydro-6-(4,5-dihydro-1H-imidazol-2-y)-1-(methylthio)-3H-benz[e]indole The product from Example 123 (1.9 g) was dissolved in methylene chloride (35 ml) and methanol (1.5 ml) and reacted with ethylenediamine (3.5 ml) as in Example 35 giving the desired product (1.38 g).

EXAMPLE 125

6,7,8,9-Tetrahydro-6-(4,5-dihydro-1H-imidazol-2-yl)-3H-benz[e]indole fumarate

The product from Example 124 (1 g) was dissolved in ethanol (150 ml) and then treated with Raney nickel (2 g) at room temperature for 4 hours. The catalyst was filtered and the filtrate was evaporated to dryness. The residue was dissolved in cold 5% sodium hydroxide solution and was extracted with methylene chloride. The organic layer was separated, dried and evaporated to dryness. The residue was dissolved in ethanol (25 ml), then treated with a solution of fumaric acid (0.24 g) in ethanol (10 ml) and the solution was diluted with ether until cloudy. The resulting fumarate salt was filtered and dried affording the product in 50% yield; m.p. 276°–79° C.

EXAMPLE 126

3-Methyl-5-nitrobenzaldehyde

A mixture of nitroxylene (150 g), N-bromo succinimide (160 g) and benzoylperoxide (4.8 g) in carbontetrachloride (1200 ml) was heated to reflux for 4 hours with a mechanical stirrer. The precipitated succinimide was filtered and the filtrate evaporated. The oily residue was dissolved in chloroform (800 ml) and bistetrabutyl ammonium chromate (420 g) was added. The solution was refluxed for 3 hours, cooled to room temperature and diluted with benzene (500 ml) and filtered. The salts were washed with ethyl acetate until no desired material appeared on thin layer chromatography. The combined organic layer was evaporated and the residue, after chromatography, afforded the desired aldehyde in 50% yield. m.p. 81°-82° C.

EXAMPLE 127

γ-Chloro-3-methyl-5-nitrobenzenebutanoic acid ethyl ester

To a solution of 1-ethoxy-1-trimethylsilyl oxycyclopropane (12 g) in methylene chloride (100 ml) at 0° C. was added a solution of titanium tetrachloride in methylene chloride (1M, 55 ml). The reaction mixture turned to a homogeneous wine-red solution with evolution of heat. The reaction was warmed to room temperature for 30 minutes and cooled back to −50° C. Then a solution of the product from Example 126 (6 g) in methylene chloride (50 ml) was added. The reaction mixture was allowed to warm to room temperature, stirred for 1.5 hours and quenched with saturated ammonium chloride solution. The organic layer was separated, washed with brine, dried, and evaporated affording the desired product (9.4 g) in 96% yield.

EXAMPLE 128

3-(Acetylamino)-5-methylbenzenebutanoic acid ethyl ester

The product from Example 127 (10 g) was hydrogenated using the procedure of Example 102 affording the desired product in 90% yield.

EXAMPLE 129

3-Acetylamino-5-methylbenzenebutanoic acid

Using the procedure of Example 101 the product from Example 128 was hydrolyzed to afford the desired acid in 100% yield.

EXAMPLE 130

6-Acetylamino-8-methyl-1-tetralone

The product from Example 129 (3 g) was treated with a solution of trimethylsilyl polyphosphate (PPSE) (50 ml in o-dichlorobenzene) at 100° C. for 10 minutes. The reaction was cooled to 0° C., quenched with 2NHCl and extracted with methylene chloride. The organic layer was separated, dried and evaporated to one-half the volume and purified on a small bed of silica gel. The desired tetralone was obtained in 40% yield. m.p.

EXAMPLE 131

6-Amino-8-methyl-1-tetralone

The product from Example 130 (2.35 g) was hydrolyzed with 6NHCl (50 ml) at reflux for 30 minutes. The procedure of Example 82 was then followed, affording the desired product in 100% yield.

EXAMPLE 132

6-Amino-5,7-dichloro-8-methyl-1-tetralone

A solution of the product from Example 130 (1.78 g) in chloroform (50 ml) at −78° C. was treated with t-butylhypochlorite (2 ml) in two portions. The reaction was stirred at −78° C. for 10 minutes. Following the procedure of Example 95 the desired product was obtained in 50% yield.

EXAMPLE 133

6-Amino-1-cyano-5,7-dichloro-8-methyl-(3,4-dihydronaphthalene)

Utilizing the procedure of Example 1 but replacing the 5,6-dimethoxy-1-tetralone with the product from Example 132 (1 g) afforded the desired compound in 90% yield.

EXAMPLE 134

6-Amino-1-cyano-5,7-dichloro-8-methyl-(1,2,3,4-tetrahydronaphthalene)

The product from Example 133 (1 g) was reduced using the procedure of Example 2 to afford the product in 98% yield.

EXAMPLE 135

6-Amino-5,7-dichloro-8-methyl-1,2,3,4-tetrahydronaphthalene-1-carboxylic acid

A solution of the product from Example 134 (0.46 g) in 12N hydrochloric acid was refluxed for 50 hours. The reaction mixture was evaporated to dryness to afford the desired acid in 100% yield.

EXAMPLE 136

6-Amino-5,7-dichloro-8-methyl-1,2,3,4-tetrahydronaphthalene-1-carboxylic acid, methyl ester The product from Example 135 (0.5 g) was dissolved in methanol (50 ml) and concentrated sulfuric acid (3 ml) was added. The reaction was refluxed for 4 hours and solvent was evaporated to one-half the volume. The concentrated reaction mixture was diluted with benzene (50 ml) and washed with brine, and aqueous sodium bicarbonate. The organic layer was separated, dried and evaporated affording the desired ester in 89% yield.

EXAMPLE 137

2-(6-Amino-5,7-dichloro-1,2,3,4-tetrahydro-8-methyl-1-naphthalenyl)imidazoline HCl Ethylenediamine (0.53 ml) was added dropwise to a stirred solution of trimethyl aluminum (4 ml) in 50 ml xylene at 0° C. under an atmosphere of nitrogen. At the end of methane evolution a solution of the product from Example 136 (0.41 g) in xylene (10 ml) was added. The reaction mixture was refluxed for 24 hours. After cooling, the solution was treated with water (10 ml), methanol (20 ml) and the solvent evaporated to one-half volume. The solution was diluted with water, and extracted with methylene chloride. The organic layer was dried and evaporated and the oily residue was purified by column chromatography affording the desired compound in 56% yield. The solid was dissolved in methanol and ethereal hydrochloric acid, affording the desired hydrochloride salt. m.p. 218°-21° C.

EXAMPLE 138

8-Amino-1-cyano-6-methyl-(3,4-dihydronaphthalene)

Utilizing the procedure of Example 1 but replacing the 5-methoxy-1-tetralone with 8-amino-6-methyl-1-tetralone afforded the desired product in 70% yield.

EXAMPLE 139

8-Amino-1-cyano-6-methyl-(1,2,3,4-tetrahydronaphthalene)

The product from Example 138 was reduced using the procedure of Example 2 to afford the desired material in 70% yield.

EXAMPLE 140

8-Amino-6-methyl-1,2,3,4-tetrahydronaphthalene-1-carboxylic acid

A solution for the product from Example 139 in 12N hydrochloric acid was refluxed for 30 hours. The reaction mixture was evaporated to dryness to afford the desired acid in 100% yield.

EXAMPLE 141

8-Amino-6-methyl-1,2,3,4-tetrahydronaphthalene-1-carboxylic acid, methyl ester

The product from Example 140 was dissolved in methanol (50 ml) and concentrated sulfuric acid (3 ml) was added. The reaction was refluxed for 4 hours and solvent was evaporated to one-half the volume. Following the procedure of Example 136 the desired ester was obtained.

EXAMPLE 142

2-(8-Amino-1,2,3,4-tetrahydro-6-methyl-1-naphthalenyl)imidazoline-2HCl

Using the product from Example 141 and the procedure from Example 137 afforded the desired compound.

EXAMPLE 143

6-Amino-1-cyano-5,7-dichloro-(3,4-dihydronaphthalene)

Utilizing the procedure of Example 1 but replacing the 5,6-dimethoxy-1-tetralone with the product 6-amino-5,7-dichloro-1-tetralone (10 g) afforded the desired compound in 90% yield.

EXAMPLE 144

6-Amino-1-cyano-5,7-dichloro-(1,2,3,4-tetrahydronaphthalene)

The product from Example 143 (10 g) was reduced using the procedure of Example 2 to afford the product in 98% yield.

EXAMPLE 145

2-(6-Amino-5,7-dichloro-1,2,3,4-tetrahydro-1-naphthalenyl)imidazoline HCl

Utilizing the procedure of Example 74 with 6-amino-5,7-dichloro-(1,2,3,4-tetrahydronaphthalene) (4.2 g) and ethylenediamine (5 ml) gave the desired compound in 50% yield. m.p. 286°–88° C.

EXAMPLE 146

6-Amino-5-chloro-1-cyano-(3,4-dihydronaphthalene)

Utilizing the procedure of Example 1 but replacing the 5,6-dimethoxy-1-tetralone with 6-amino-5-chloro-1-tetralone (3 g) afforded the desired compound in 90% yield.

EXAMPLE 147

6-Amino-5-chloro-1-cyano-1-(1,2,3,4-tetrahydronaphthalene)

The product from Example 146 (3 g) was reduced using the procedure of Example 2 to afford the product in 98% yield.

EXAMPLE 148

2-(6-Amino-5-chloro-1,2,3,4-tetrahydro-1-naphthalenyl)imidazoline HCl

Utilizing the procedure of Example 74 with 6-amino-1-cyano-5-chloro-(1,2,3,4-tetrahydronaphthalene) (1.2 g) and ethylenediamine (3 ml) gave the desired compound in 60% yield. m.p. 220° C. (decomp.).

The selectivity of the compounds can be demonstrated in vitro by testing the compounds on isolated tissues such as stimulated rabbit aorta strips and by radioligand binding studies. The therapeutic activity of the compounds can be demonstrated in vivo by the compounds ability to affect arterial blood pressure and/or heart rate in various experimental animals such as the spontaneously hypertensive (SH) rat.

In the latter test, a group of SH male rats are trained to be restrained in a wire mesh cylinder in a warming box, at least two training cycles being conducted before testing. The rats are warmed for about one-half hour period to blood pressure measurement, the warming box being maintained at a constant temperature of 36° C. An occluding cuff attached to a programmed sphymomanometer is placed near the base of the tail of each rat and the pressure in the cuff is increased automatically from 0 to 250 millimeters of mercury (mm Hg) at a rate of 10 mm Hg per second. The total time for each cycle of inflation and deflation of the cuff is 50 seconds and the interval between cycles is one minute. A photocell is placed distal to the cuff to record the pulses due to forward motion of blood flow with each heart beat. As the pressure in the cuff increases, the pulse disappears completely at a point where cuff pressure equals or exceeds the arterial blood pressure and it reappears during deflation at approximately the same pressure. Five interference free signals for deflation are recorded for each rat. Rats with a blood pressure of 180 mm Hg or more during the control period are used in the study. Blood pressure and heart rate readings are recorded on a Model VII Grass polygraph at various intervals after administration of the test compound. When tested in accordance with the foregoing procedure, the preferred compounds of the invention have decreased the arterial blood pressure and/or heart rate of rats of the group.

The compounds of the invention can be administered in any effective pharmaceutically acceptable form to warm blooded animals, e.g., in oral, parenteral or infusable dosage forms, or as a buccal or nasal spray. Suitable parenteral routes of administration include, for example, intramuscular, intravenous, intraperitoneal or subcutaneous administration of the compounds.

In addition to the active compounds, compositions according to this invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or other sterile injectable medium, immediately before use.

Solid dosage forms for oral administration include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions may also comprise adjuvants, such as wetting agents, emulsifying and suspending agents, and sweetening, flavoring and perfuming agents.

Actual dosage levels of active ingredient in the compositions of the invention may be varied so as to obtain an amount of active ingredient effective to obtain a desired therapeutic response for a particular composition and method of administration. The selected dosage level therefore depends upon the desired therapeutic effect, on the route of administration, on the desired duration of treatment and other factors. Generally, dosage levels of about 0.1 to about 200, more preferably about 0.5 to about 150 and most preferably about 1 to about 125 mg of active ingredient per kg of body weight per day are administered orally to a mammalian patient suffering from hypertension. If desired, the daily dose may be divided into multiple doses for administration, e.g., two to four separate doses per day.

The foregoing is merely illustrative of the invention and is not intended to limit the invention to the disclosed compounds. Variations and changes which are obvious to one skilled in the art are intended to be within the scope and nature of the invention which are defined in the appended claims.

We claim:

1. A compound of the formula

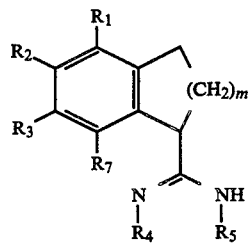

wherein m is 0, 1 or 2; $R_1$, $R_2$, $R_3$ and $R_7$ are taken from the group consisting of hydrogen, hydroxy, loweralkyl, loweralkoxy, halo, amino, acetamido or $NHSO_2R$ wherein R is taken from the group consisting of hydrogen or loweralkyl, provided that $R_1$, $R_2$, $R_3$ and $R_7$ cannot simultaneously be hydrogen or halo, and provided that when one of $R_1$, $R_2$, $R_3$ and $R_7$ is halo, the others cannot simultaneously be hydrogen and when two of $R_1$, $R_2$, $R_3$ and $R_7$ are halo, the other two cannot simultaneously be hydrogen and when three of $R_1$, $R_2$, $R_3$ and $R_7$ are halo, the other cannot simultaneously be hydrogen, and provided that $R_1$ and $R_7$ cannot simultaneously be methoxy each when $R_2$ and $R_3$ are hydrogen; $R_1$ and $R_2$ or $R_2$ and $R_3$ or $R_3$ and $R_7$ taken together can form a methylenedioxy or ethylenedioxy ring, or $R_1$ and $R_2$ or $R_2$ and $R_3$ or $R_3$ and $R_7$ taken together with the aromatic ring can form a benzimidazole or indole ring; and $R_4$ and $R_5$ are hydrogen or taken together form a closed ring of the formula

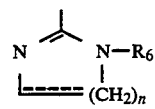

wherein n is 1 or 2, and the combined solid and dashed line represents a single or double bond when n is 1, and $R_6$ is taken from the group consisting of hydrogen or loweralkyl, or a pharmaceutically acceptable salt thereof.

2. The compound in accordance with claim 1 wherein m is 1 and n is 1.

3. The compound in accordance with claim 1 wherein m is 2 and n is 1.

4. The compound in accordance with claim 1 wherein m is 2 and n is 2.

5. The compound in accordance with claim 2 wherein $R_1$ and $R_2$ are each hydroxy.

6. The compound in accordance with claim 3 wherein $R_1$ and $R_2$ are each hydroxy.

7. The compound in accordance with claim 3 wherein $R_1$ and $R_3$ are each methoxy.

8. The compound in accordance with claim 2 wherein $R_1$, $R_2$, $R_3$ and $R_7$ are taken from the group consisting of hydrogen, hydroxy or methoxy.

9. The compound in accordance with claim 2 wherein $R_1$ and $R_2$ are taken together to form a methylenedioxy ring.

10. The compound in accordance with claim 2 wherein $R_1$ and $R_2$ are each hydroxy.

11. The compound in accordance with claim 2 wherein $R_1$ and $R_2$ taken together with the aromatic ring form a benzimidazole ring wherein $R_6$ is hydrogen.

12. The compound in accordance with claim 4 wherein $R_1$, $R_2$, $R_3$ and $R_7$ are taken from the group consisting of hydrogen, hydroxy or methoxy.

13. The compound in accordance with claim 4 wherein $R_1$ and $R_2$ form a methylenedioxy ring.

14. A composition with alpha-adrenergic activity in pharmaceutical dosage containing a carrier and a therapeutically effective amount of a compound of the formula of claim 1.

15. A method of treating hypertension which comprises administering to a patient a therapeutically effective amount of a compound of the formula of claim 1.

* * * * *